United States Patent
Ramakrishna et al.

[11] Patent Number: 5,900,436
[45] Date of Patent: May 4, 1999

[54] SUBSTITUTED INDANYLIDINEACETYLGUANIDINES, PROCESSES FOR THEIR PREPARATION, THEIR USE AS MEDICAMENTS OR DIAGNOSTICS AND MEDICAMENTS CONTAINING THEM

[75] Inventors: Nirogi Venkata Satya Ramakrishna; Arun Kumar Jain, both of Mulund (W) Bombay; Bansi Lal, Mulund (W) Bombay PIN; Rao Venkata Satya Veerabhadra Vadlamudi, New Bombay; Anil Vasantrao Ghate, Thane (W); Ravindra Dattatraya Gupte, Andheri (W) Bombay, all of India; Andreas Weichert, Egelsbach; Jan-Robert Schwark, Frankfurt, both of France

[73] Assignee: Hoechst Aktiengesellschaft, Main, Germany

[21] Appl. No.: 08/901,099

[22] Filed: Jul. 28, 1997

[30] Foreign Application Priority Data

Jul. 30, 1996 [EP] European Pat. Off. ............ 96112275

[51] Int. Cl.$^6$ ............... A61K 31/165; C07C 231/02; C07C 233/09
[52] U.S. Cl. ............... 514/617; 514/619; 514/522; 514/821; 558/414; 564/161; 564/163; 564/166; 564/172; 564/180; 564/142
[58] Field of Search ........................... 564/180, 142, 564/161, 163, 166, 172; 514/617, 821, 619, 522; 558/414

[56] References Cited

U.S. PATENT DOCUMENTS 5,091,394  2/1992  Englert et al. .................... 514/331

FOREIGN PATENT DOCUMENTS 0 688 766  12/1995  European Pat. Off. .

Primary Examiner—Shailendra Kumar
Attorney, Agent, or Firm—Finnegan, Henderson, Farabow, Garrett & Dunner, L.L.P.

[57] ABSTRACT

Substituted Indanylidineacetylguanidines, process for their preparation, their use as medicaments or diagnostic and medicaments containing them:

Indanylidineacetylguanidines I

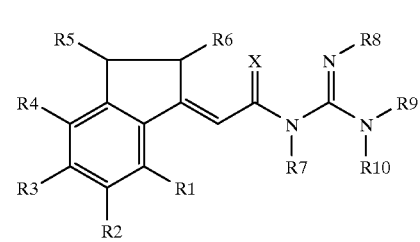

and their pharmaceutically acceptable salts wherein R1, R2, R3, R4, R5, R6, R7, R8, R9, R10 and X have the meanings given in the claims, are effective inhibitors of the cellular sodium/proton antiport (Na$^+$/H$^+$exchanger), which, in numerous diseases (essential hypertension, atherosclerosis, diabetes and the like) is also increased in those cells which are readily accessible for measurements, such as, for example, in erythrocytes, platelets or leukocytes. They are also advantageous for the preparation of a medicament for the treatment or prophylaxis of disorders of lipid metabolism.

15 Claims, No Drawings

SUBSTITUTED INDANYLIDINEACETYLGUANIDINES, PROCESSES FOR THEIR PREPARATION, THEIR USE AS MEDICAMENTS OR DIAGNOSTICS AND MEDICAMENTS CONTAINING THEM

SUMMARY OF THE INVENTION

The present invention relates to Indanylidineacetylguanidines, process for their preparation, their use as medicaments, their use as diagnostic agents and medicaments containing them. The Indanylidineacetylguanidines of the invention have the formula I:

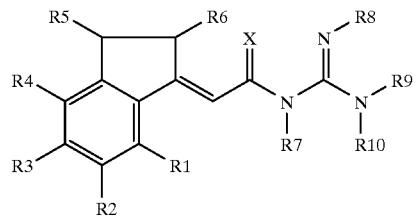

wherein,

R1, R2, R3, R4, R5 and R6 individually or collectively represent H, $C_1$–$C_{10}$-alkyl, haloalkyl having 1–6 carbon atoms, O—$C_1$–$C_{10}$-alkyl, haloalkoxy having 1–6 carbon atoms, halogens such as F, Cl, Br, I, aryl, substituted aryl, heteroaryl, substituted heteroaryl, OH; O-lower alkyl, O-aryl, O-lower alkyl aryl, O-substituted aryl, O-lower alkyl-substituted aryl, O—C(=O)—$C_1$–$C_4$-alkyl-aryl, O—C(=O)—NH—$C_1$–$C_4$-alkyl, O—C(=O)—N($C_1$–$C_4$-alkyl)$_2$, NO$_2$, CN, CF$_3$, NH$_2$, NH—C(=O)—$C_1$–$C_4$-alkyl, NH—C(=O)—NH$_2$, COOH, C(=O)—O—$C_1$–$C_4$-alkyl, C(=O)—NH$_2$, C(=O)—NH—$C_1$–$C_4$-alkyl, C(=O)—N($C_1$–$C_4$-alkyl)$_2$, $C_1$–$C_4$—COOH, $C_1$–$C_4$-alkyl-C(=O)—O—$C_1$–$C_4$-alkyl; SO$_3$H; SO$_2$-alkyl, SO$_2$-alkylaryl, SO$_2$—N-(alkyl)$_2$, SO$_2$—N(alkyl)(alkylaryl), C(=O)—R$_{11}$, $C_1$–$C_{10}$-alkyl-C(=O)—R$_{11}$, $C_2$–$C_{10}$-alkenyl-C(=O)—R$_{11}$, $C_2$–$C_{10}$-alkynyl-C(=O)—R$_{11}$, NH—C(=O)—$C_1$–$C_{10}$-alkyl-C(=O)—R$_{11}$ or O—$C_1$–$C_{11}$-alkyl-C(=O)—R$_{11}$, R$_{11}$ is $C_1$–$C_4$ alkyl, $C_1$–$C_4$-alkynyl, aryl substituted aryl, NH$_2$, NH—$C_1$–$C_4$-alkyl, N—($C_1$–$C_4$-alkyl)$_2$, SO$_3$H, SO$_2$-alkyl, SO$_2$-alkylaryl, SO$_2$—N-(alkyl)$_2$ or SO$_2$—N(alkyl)(alkylaryl);

X is O, S or NH;

R7, R8, R9 and R10 are individually or collectively H, alkyl, cycloalkyl, aryl or alkylaryl; or R8, R9 together are part of a 5-, 6- or 7-membered heterocyclic ring; or their salt with a nontoxic organic or mineral acid.

DETAILED DESCRIPTION OF THE INVENTION

The disclosure of German Application No. 96112275.1 filed Jul. 30, 1996 is hereby incorporated by reference.

Exemplary non toxic, pharmaceutically acceptable acids A are hydrochloric acid, hydrobromic acid, sulfuric acid, nitric acid, phosphoric acid, methanesulfonic acid, benzene sulfonic acid, toluene sulfonic acid, acetic acid, lactic acid, salicylic acid, benzoic acid, nicotinic acid, phthalic acid, stearic acid, oleic acid and oxalic acid.

Throughout this disclosure, the following terms, unless otherwise indicated, shall be understood to have the following meanings:

"Alkyl" means a saturated aliphatic hydrocarbon which may be either straight- or branched-chain. Preferred alkyl groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to about 6 carbon atoms. Examples of lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group. Preferred groups have about 3 to about 6 carbon atoms, and exemplary groups include cyclopropyl, cyclopentyl and cyclohexyl. "Alkenyl" means an unsaturated aliphatic hydrocarbon. Preferred groups have no more than about 12 carbon atoms. Exemplary groups include any structural and geometric isomers of ethenyl, propenyl, butenyl, pentenyl, hexenyl, heptenyl, octenyl, nonenyl, decenyl, undecenyl and dodecenyl or butadienyl, pentadienyl etc.

"Lower alkenyl" means alkenyl of about 2 to 6 carbon atoms. Preferred groups include ethenyl, propenyl, butenyl, isobutenyl, and all structural and geometrical isomers thereof.

"Alkynyl" means an unsaturated aliphatic hydrocarbon. Preferred groups have no more than about 12 carbon atoms and contain one or more triple bonds, including any structural or isomers of ethynyl, propynyl, butynyl, pentynyl, hexynyl, heptynyl, octynyl, nonynyl, decynyl, undecynyl, dodecynyl, etc.

"Lower alkynyl" means alkynyl of about 2 to 6 carbon atoms. Preferred groups include structural isomers of propynyl, butynyl, and pentynyl.

"Aryl" means phenyl and substituted phenyl.

"Substituted Phenyl" means a phenyl group in which one or more of the hydrogens have been replaced by the same or different substituents including halo, lower alkyl, lower alkenyl, lower alkynyl, halo-lower alkyl, nitro, amino, acylamino, hydroxy, carboxyl, lower alkoxy, aryl lower alkoxy, acyloxy lower alkanoyl, cyano, amido, loweralkylamino, lower alkoxy-amino, aralkyl-amino, or loweralkyl-sulfonyl.

"Aralkyl" means an alkyl group in which one or more hydrogens have been substituted by an aryl group. Preferred groups are phenalkyl and substituted phenalkyl.

"Phenalkyl" means an alkyl group substituted by a phenyl group.

"Substituted phenalkyl" means a phenalkyl group in which one or more phenyl hydrogen are replaced as given above with respect to substituted phenyl.

"Substituted phenalkenyl" mean a phenalkenyl group in which the phenyl group is substituted as given above with respect to substituted phenyl.

"Heterocyclic ring" or "heterocycle" means a 3, 5, 6 or 7 membered ring having 1 to 3 hetero atoms which may be nitrogen, oxygen or sulfur, including pyrrole, pyrrolidine, pyridone, heptamethyleneiminyl, pyrazole, pyridyl, pyrimidyl, pyrazolyl, imidazolyl, isoxazolyl, furyl, thienyl, oxazolyl, thiazolyl, piperidyl, morpholinyl, oxazolidinyl, thiazolidinyl, pyrazolidinyl, imidazolidinyl, piperazinyl, thiamorpholinyl, azepinyl and ethyleneiminyl.

"Substituted heterocycle" means a heterocycle in which one or more of the hydrogens on the ring carbons have been replaced by substituents as given above with respect to substituted phenyl.

The term "halo" and "halogen" include all four halogens; namely fluorine, chlorine, bromine and iodine. The halo alkyls, halophenyl and halo-substituted pyridyl groups having more than one halo substituent which may be the same or different such as trifluoromethyl, 1-chloro-2-bromo-ethyl, chlorophenyl, and 4-chloropyridyl.

"Acyl" means an organic carbonyl radical of a lower alkanoic acid. Preferred acyl groups are lower alkanoyl groups such as acetyl and propionyl.

"Aroyl" means an aromatic acid radical such as benzoyl, toluoyl.

"Lower alkanoyl" means the acyl radical of a lower alkanoic acid such as acetyl, propionyl, butyryl, valeryl, stearoyl and the like.

"Alkoxy" means an alkyloxy group and includes hydroxy alkyl groups. Preferred lower alkoxy groups are methoxy, ethoxy, n-propoxy and isopropoxy, isobutoxy, n-butoxy and t-butoxy.

Preferred compounds of the invention are compounds of formula II.

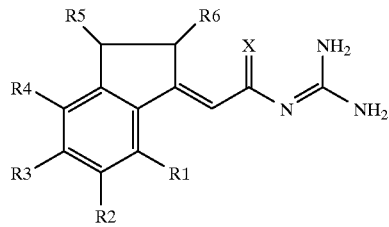

wherein,

R1, R2, R3, R4, R5 and R6 individually or collectively represent H, $C_1$–$C_{10}$-alkyl, haloalkyl having 1–6 carbon atoms, O—$C_1$–$C_{10}$-alkyl, haloalkoxy having 1–6 carbon atoms, halogens such as F, Cl, Br, I, aryl, substituted aryl, heteroaryl, substituted heteroaryl, OH, O-lower alkyl, O-aryl, O-lower alkyl aryl, O-substituted aryl, O-lower alkyl-substituted aryl, O—C(=O)—$C_1$–$C_4$-alkyl-aryl, O—C(=O)—NH—$C_1$–$C_4$-alkyl, O—C(=O)—N($C_1$–$C_4$-alkyl)$_2$, NO$_2$, CN, CF$_3$, NH$_2$, NH—C(=O)—$C_1$–$C_4$-alkyl, NH—C(=O)—NH$_2$, COOH, C(=O)—O—$C_1$–$C_4$-alkyl, C(=O)—NH$_2$, C(=O)—NH—$C_1$–$C_4$-alkyl, C(=O)—N($C_1$–$C_4$-alkyl)$_2$, $C_1$–$C_4$—COOH, $C_1$–$C_4$-alkyl-C(=O)—O—$C_1$–$C_4$-alkyl, SO$_3$H, SO$_2$-alkyl, SO$_2$-alkylaryl, SO$_2$—N-(alkyl)$_2$, SO$_2$—N(alkyl) (alkylaryl), C(=O)—R$_{11}$, $C_1$–$C_{10}$-alkyl-C(=O)—R$_{11}$, $C_2$–$C_{10}$-alkenyl-C(=O)—R$_{11}$, $C_2$–$C_{10}$-alkynyl-C (=O)—R$_{11}$, NH—C(=O)—$C_1$–$C_{10}$-alkyl-C(=O)—R$_{11}$, O—$C_1$–$C_{11}$-alkyl-C(=O)—R$_{11}$;

R$_{11}$ is $C_1$–$C_4$ alkyl, $C_1$–$C_4$-alkynyl, aryl substituted aryl, NH$_2$, NH—$C_1$–$C_4$-alkyl, N—($C_1$–$C_4$-alkyl)$_2$, SO$_3$H, SO$_2$-alkyl, SO$_2$-alkylaryl, SO$_2$—N-(alkyl)$_2$, SO$_2$—N(alkyl)(alkylaryl), X is O, S or NH but preferably X is oxygen; and their pharmaceutically acceptable salts.

The compounds of the present invention contain geometric isomers, the invention relates to both E and Z isomers. The compounds of the present invention may contain asymmetric centers, the invention relates to both compounds of the S and of the R configuration. The compounds can exist as optical isomers, as racemates or as mixtures thereof.

According to the invention there is also provided a process for the preparation of a compound of the formula I which comprises reacting a compound of the formula V

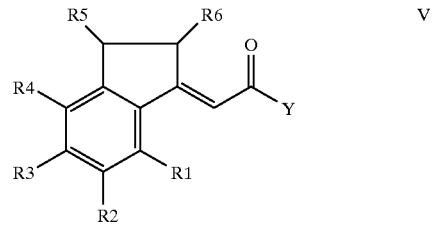

in which

R1, R2, R3, R4, R5 and R6 are as defined above and
Y is a leaving group selected from O—($C_1$–$C_4$)-alkyl, halogen or imidazolyl, with a guanidine of the formula VI

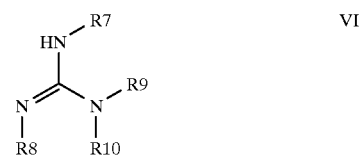

wherein

R7, R8, R9 and R10 are as defined above and if desired converting the product into pharmaceutically tolerated salts.

Representative examples of the compounds of this invention are listed in Table 1.

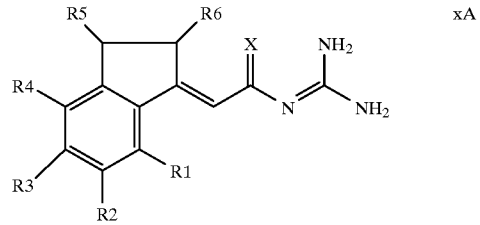

wherein:

R5 and R6 are H; and X is oxygen; A is CH$_3$SO$_3$H.

TABLE 1

| Compound No. | R$_1$ | R$_2$ | R$_3$ | R$_4$ | M.P. [°C.] |
|---|---|---|---|---|---|
| 1. | H | CH$_3$ | H | H | 209–210 |
| 2. | H | H | H | H | 235–236 |
| 3. | H | Cl | H | H | 196–197 |
| 4. | H | H | H | CH$_3$ | 225–226 |
| 5. | H | F | H | H | 215–216 |
| 6. | H | OCH$_3$ | H | H | 204–205 |
| 7. | H | H | CH$_3$ | H | 216–217 |
| 8. | CH$_3$ | H | H | H | 245–246 |
| 9. | CH$_3$ | H | H | CH$_3$ | 248–249 |

The compounds of formula I are substituted acylguanidines. The most prominent representatives of the acylguanidines is the pyrazine derivative amiloride, which is used in therapy as a calcium-saving diuretic. Numerous other compounds of the amiloride type are described in the literature, such as, for example, dimethylamiloride or ethylisopropylamiloride. Studies which indicate antiarrhythmic properties of amiloride moreover have been disclosed [Circulation 79, 1257–1263 (1989)]. However, wide use as an antiarrhythmic is impeded by the fact that this effect is only slight and occurs accompanied by an antihypertensive and saluretic action and these side effects are undesirable in the treatment of disturbances in cardiac rhythm.

Indications of antiarrhythmic properties of amiloride have also been obtained from experiments on isolated animal hearts [Eur. Heart J. 9 {supplement 1}: 167 (1988) (book of abstracts)]. Thus, for example, it has been found on rat hearts that it was possible to suppress an artificially induced ventricular fibrillation completely by amiloride. The above mentioned amiloride derivative ethylisopropylamiloride was even more potent than amiloride in this model.

Benzoyl guanidines having antiarrhythmic properties are described in European Offenlegungsschrift 416 499.

U.S. Pat. No. 3,780,027 also describes acylguanidines, which differ fundamentally from the compounds of formula I according to the invention described here in that they are trisubstituted benzoyl guanidines which are derived in their substitution pattern from commercially available diuretics, such as bumetanide and furosemide and have an amino group, which is important for the salidiuretic action sought, in position 2 or 3 relative to the carbonyl guanidine group. A potent salidiuretic activity is correspondingly reported for these compounds. It was therefore surprising that the compounds according to the invention have no undesirable and adverse salidiuretic properties but very good antiarrhythmic properties, so they can be used for the treatment of health disorders, such as oxygen deficiency symptoms. As the result of their pharmacological properties, the compounds are outstandingly suitable as antiarrhythmic medicaments having a cardioprotective component for prophylaxis of infarction and treatment of infarction and for treatment of angina pectoris, where they also preventively inhibit or greatly reduce the pathophysiological processes in the development of ischemically induced damage, in particular the initiation of ischemically induced cardiac arrhythmias. Because of their protective actions against pathological hypoxic and ischemic situation, the compounds of the formula I according to the invention, as a result of inhibition of the cellular $Na^+/H^+$ exchange mechanism, can be used as medicaments for the treatment of all acute or chronic damage caused by ischemia or diseases thereby induced primarily or secondarily. This applies to their use as medicaments for surgical interventions, for example organ transplants, where the compounds can be used both for protection of the organs in the donor before and during removal, for protection of organs removed, for example during treatment with or storage thereof in physiological bath fluids, and also during transfer to the recipient organism. The compounds are also valuable medicaments which have a protective action while angioplastic surgical interventions are carried out, for example on the heart and also on peripheral vessels. In accordance with their protective action against ischemically induced damage, the compounds are also suitable as medicaments for the treatment of ischemias of the nervous system, in particular the CNS, where they are suitable, for example, for the treatment of apoplexy or cerebral edema. The compounds of the formula I according to the invention moreover are also suitable for treatments of forms of shock, such as, for example, allergic, cardiogenic, hypovolemic and bacterial shock.

The compounds of the formula I according to the invention furthermore are distinguished by a potent inhibiting action on the proliferation of cells, for example fibroblast cell proliferation and proliferation of smooth vascular muscle cells. The compounds of the formula I are therefore possible valuable therapeutics for diseases in which cell proliferation is a primary or secondary cause, and they can therefore be used as antiatheroscerotics and as agents delayed diabetic complications, cancer diseases, fibrotic diseases, such as pulmonary fibrosis, hepatic fibrosis or renal fibrosis, and organ hypertrophies and hyperplasias, in particular prostate hyperplasia or prostate hypertrophy.

The compounds according to the invention are effective inhibitors of the cellular sodium/proton antiport ($Na^+/H^+$ exchanger), which, in numerous diseases (essential hypertension, atherosclerosis, diabetes and the like) is also increased in those cells which are readily accessible for measurements, such as, for example, in erythrocytes, platelets or leukocytes. The compounds according to the invention are therefore suitable as outstanding and simple scientific tools, for example in their use as diagnostics for determination and differentiation of certain forms of hypertension, but also of atherosclerosis, diabetes, proliferative diseases and the like. The compounds of the formula I furthermore are suitable for preventive therapy for prevention of the origin of high blood pressure, for example essential hypertension.

It has additionally been found that compounds of the formula I have a favorable effect on serum lipoproteins. It is generally recognized that for the formation of arteriosclerotic vascular changes, in particular of coronary heart disease, excessively high blood lipid values, so-called hyperlipoproteinemias, are a significant risk factor. For the prophylaxis and the regression of atherosclerotic changes, the lowering of raised serum lipoproteins is therefore of extreme importance. Beside the reduction of the total serum cholesterol, the lowering of the proportion of specific atherogenic lipid fractions of this total cholesterol, in particular of the low density lipoproteins (LDL) and of the very low density lipoproteins (VLDL) is of particular importance, as these lipid fractions are an atherogenic risk factor. In contrast, the high density lipoproteins are ascribed a protective function against coronary heart disease. Accordingly, hypolipidemics should be able not only to lower the total cholesterol, but in particular the VLDL and LDL serum cholesterol fractions. It has now been found that compounds of the formula I have valuable therapeutically utilizable properties with respect to the effect on the serum lipid levels. Thus they significantly lower the raised serum concentrations of LDL and VLDL, as are to be observed, for example, as a result of increased dietetic uptake of a cholesterol- and lipid-rich diet or in the case of pathological metabolic changes, for example genetically related hyperlipidemias. They can therefore be used for the prophylaxis and for the regression of atherosclerotic changes in that they eliminate a causal risk factor. These include not only the primary hyperlipidemias, but also certain secondary hyperlipidemias, such as occur, for example, in diabetes. Moreover, the compounds of the formula I lead to a marked reduction of the infarcts induced by metabolic anomalies and in particular to a significant decrease in the induced infarct size and its degree of severity.

Furthermore, compounds of the formula I result in effective protection against damage due to metabolic anomalies of induced endothelial damage. With this protection of the vessels against the syndrome of endothelial dysfunction, compounds of the formula I are valuable medicaments for the prevention and for the treatment of coronary vascular spasms, of atherogenesis and of atherosclerosis, of left-ventricular hypertrophy and of dilated cardiomyopathy, and of thrombotic disorders.

The compounds mentioned are therefore advantageously used for the production of a medicament for the treatment of hypercholesterolemia; for the production of a medicament for the prevention of atherogenesis; for the production of a medicament for the prevention and treatment of atherosclerosis, for the production of a medicament for the prevention and treatment of illnesses which are induced by raised cholesterol levels, for the production of a medicament for the prevention and treatment of illnesses which are induced by endothelial dysfunction, for the production of a medicament for the prevention and treatment of atherosclerosis-induced hypertension, for the production of a medicament for the prevention and treatment of atherosclerosis-induced thromboses, for the production of a medicament for the prevention and treatment of hypercholesterolemia and endothelial dysfunction-induced ischemic damage and postischemic reperfusion damage, for the production of a medicament for the prevention and treatment of hypercholesterolemia and endothelial dysfunction-induced cardiac hypertrophies and cardiomyopathies, for the production of a medicament for the prevention and treatment of hypercholesterolemia and endothelial dysfunction-induced coronary vascular spasms and myocardial infarcts, for the production of a medicament for the treatment of the conditions mentioned in combinations with hypotensive substances, preferably with angiotensin converting enzyme (ACE) inhibitors and angiotensin receptor antagonists, a combination of an NHE inhibitor of the formula I with a blood lipid level-lowering active compound, preferably with an HMG-CoA-reductase inhibitor (e.g. lovastatin or pravastatin), the latter contributing a hypolipidemic action and thereby increasing the hypolipidemic properties of the NHE inhibitor of the formula I, proving to be a favorable combination with increased action and decreased use of active compound.

This invention also relates to the process for preparation of compounds of formula 1. The preparation of the compounds of the invention are illustrated, but not limited, by preparation of exemplary compounds of the invention.

The synthesis of compounds of formula I was achieved through intermediate of formula III,

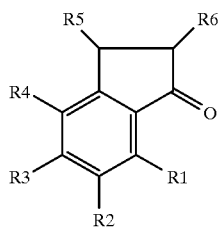

in which

R1, R2, R3, R4, R5 and R6 are as defined above. The compounds of formula III are made through known methods. One of the methods is by cyclizing 3-phenylpropanoic acid using polyphosphoric acid. Compounds of formula III are converted into acids of formula IV,

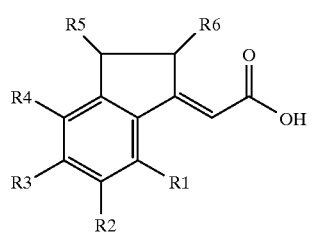

wherein R1, R2, R3, R4, R5 and R6 are as defined above, on treatment with Wittig reagent $(Ph)_3P^+=CHCOOEt.Br^-$ at temperatures of from 200 to 250° C. in neat for 10–12 hours and subsequent work-up.

The activated acid derivatives of the formula V in which Y is an alkoxy group, preferably a methoxy group, an activated phenoxy group, a phenylthio, methylthio, 2-pyridylthio group or a nitrogen heterocycle, such as imidazolyl, which can be prepared from acid chloride (formula V; Y=Cl) which in turn can be prepared from acid, formula IV on treatment with thionyl chloride. Other activating ester methods can be used, which are known in peptide area to activate the acid for coupling reaction. The imidazolides of formula V, Y=imidazolides, can also be prepared from a compound of formula IV, by treating it with 1,1'-carbonyldiimidazole [C. Staab, Angew. Chem. Int. Eng Edn. 351–367 (1962)]. Compound of formula V (Y=Cl) on treatment with the compound of formula VI under Schotten-Baumann condition, also gives compound of formula I. Other mixed anhydride related to formula V may be prepared, such as with ClCOOEt, tosyl chloride, triethylphosphoryl chloride in the presence of triethylamine or any other base in an inert solvent. Activation of the COOH group in the compounds of the formula IV can also be achieved with DCC. Other methods of preparation of activated carboxylic acid derivative of formula V type are given with indication of source lit. in J. March, Advanced Organic Chemistry, 3rd Edition (John Wiley & Son, 1985), p. 350. Coupling reaction between compounds of formula V and VI can be conducted in variety of ways in protic or aprotic polar solvents, but inert organic solvents are preferred. In this connection methanol, THF, DMF, N-methylpyrrolidone, HMPA etc., between room temperature and boiling point of these solvents have proved suitable for the reaction of the formula V (Y=OMe) with guanidine. Reaction of compounds of formula V with salt free guanidine are advantageously carried out in aprotic inert solvents such as THF, dimethoxy ethane, DMF or dioxane. In case where compound of formula IV is directly treated with carbonyldiumidazole for activating the carboxyl group, aprotic polar solvents such as DMF, dimethoxy ethane are used, followed by the addition of compound of formula VI. Compounds of the formula I may be converted into pharmacologically acceptable acid addition salts with exemplary salts as described earlier in this disclosure.

The active compounds of the present invention may be administered orally, parenterally, intravenously, rectally or by inhalation, the preferred administration being dependent on the specific clinical need of the disorder. In this connection, the compounds of formula I can also be used alone or together with pharmaceutical auxiliaries, and indeed both in veterinary and in human medicine. Which auxiliaries are suitable for the desired pharmaceutical formulation is familiar to the person skilled in the art on the basis of his expert knowledge. In addition to solvents, gel-forming agents, suppository bases, tablet auxiliaries and other active compound carriers, antioxidants, dispersants, emulsifiers, defoaming agents, flavor correctors, preservatives, solubilizers or colorants can be used.

For a form for oral use, the active compounds are mixed with the additives suitable for this purpose, such as excipients, stabilizers or inert diluents and are brought into the forms suitable of administration, such as tablets, coated tablets, hard gelatin capsules, aqueous, alcoholic or oily solutions, by the customary methods. Inert carriers which can be used are, for example, gum arabic, magnesia, magnesium carbonate, potassium phosphate, lactose, glucose or starch, in particular corn starch. In this case, preparation can take place both as dry and as moist granules. Suitable oily excipients or solvents are, for example, vegetable or animal oils, such as sunflower oil or cod liver oil.

For subcutaneous or intravenous administration, the active compounds, of desired with the substances customary for this purpose such solubilizers, emulsifiers or other auxiliaries, are brought into solution, suspension or emulsion. Possible solvents are, for example: water, physiological saline solution or alcohols, for example ethanol, propanol, glycerol, in addition also sugar solutions such as glucose or mannitol solutions, or alternatively, a mixture of the various solvents mentioned.

Pharmaceutical formulations suitable for administration in the form of aerosols or sprays are, for example, solutions, suspensions or emulsions of the active compound of formula I in pharmaceutically acceptable solvent, such as, in particular, ethanol or water, or a mixture of such solvents. If required, the formulation may also contain other pharmaceutical auxiliaries such as surfactants, emulsifiers and stabilizers and also a propellant gas. Such a preparation customarily contains the active compound in a concentration of about 0.1 to 10, in particular of about 0.3 to 3 % by weight.

The dosage of the active compound of the formula I to be administered and the frequency of administration depend on the potency and duration of action of the compounds used; and additionally also on the nature and severity of the disease to be treated and on the sex, age, weight and individual responsiveness of the mammal to be treated.

The term "Patient" means a mammal such as a dog, cat, guinea pig, mouse, rat or human being.

The terms "Treating" or "to treat" means to alleviate symptoms, eliminate the causation either on a temporary or permanent basis, or to prevent or slow the appearance of symptoms (prophylaxis).

On an average, the daily dose of a compound of the formula I in a patient of about 75 kg weight is at least 0.001 mg, preferably 0.01 mg to at most 10 mg, preferably at most 1.0 mg. In acute outbreaks of the illness, for example immediately after suffering a cardiac infarction, still higher and above all, more frequent dosages may also be necessary, for example up to 4 individual doses per day. In particular on i.v. use, for example in an infarct patient in the intensive care unit, up to 100 mg per day may be necessary.

Experimental Section

The synthesis of representative example, 4-methyl-1-indanylidineacetyl-guanidine-methanesulfonic acid (compound No. 4 of formula I in Table 1).

A. Synthesis of Compound No. 4 in Table 1 a. Synthesis of compounds with formula III 3-(2-methylphenyl)-prop-1-oic acid (14 g, 0.085 moles) mixed with polyphosphoric acid (PPA, 140 g) and the mixture was heated at 80–85° C. with mechanical stirring. After 1.0 hour the reaction mixture turned to reddish color, then it was terminated by pouring into cold water. Light yellow precipitate obtained was filtered, washed with excess of water, dried and purified by column chromatography to isolate the desired product, mp. 91° C.

IR: (KBr), cm$^{-1}$: 2910, 1700, 1600, 1450, 1370, 1260, 1040 and 790.

NMR (CDCl$_3$): d: 2.30 (s, 3H, C$\underline{H}_3$); 2.80 (m, 2H, C$\underline{H}_2$); 3.25 (m, 2H, C$\underline{H}_2$); 7–7.5 (m, 3H, Ar—$\underline{H}$).

b. Synthesis of Compounds with formula IV 4-methylindanone (4.5 g, 0.03 moles) was mixed with Ethyl triphenylphosphenoacetate (Wittig reagent, 10.4 g, 0.04 moles) in a round bottomed flask then the mixture was heated at 190–200° C. in a salt bath for 5–6 hours. The reaction was terminated and the crude was purified by column chromatography. The chromatographic product was then hydrolyzed with methanolic NaOH (2 eq.), which gave 4-methyl-1-indanylidineacetic acid, mp. 80° C.

IR: (KBr), cm$^{-1}$: 3100–2900, 1700, 1450, 1330, 1225 and 950.

NMR: (CDCl$_3$): d: 2.40 (s, 3H, CH$_3$); 3.30 (m, 2H, CH$_2$); 3.65 (m, 2H, C$\underline{H}_2$); 6.50 (s, 1 H, =C$\underline{H}$); 7.00–7.40 (m, $\overline{3H}$, Ar—$\underline{H}$).

c. Synthesis of Compounds with formula I 4-methyl-1-indanylidineacetic acid (1.0 g, 0.0053 moles) was converted into corresponding acid chloride (using SOCl$_2$). The acid chloride in THF (dry, 20 ml) was added dropwise to a free guanidine (0.9 g, 0.015 moles) suspension in THF (dry, 20 ml) with stirring at room temperature. After addition the reaction mixture was stirred for ½ hour then it was terminated (after confirming its completion on TLC) by adding ice cold water (50 ml). The product was extracted with EtOAc (3×100 ml). The EtOAc layer was dried and concentrated to get crude product which was purified by column chromatography.

4-methyl-1-indanylidineacetylguanidine-methanesulfonic acid was obtained by dissolving free base in dry EtOAc and adding 1.0 equivalent of methanesulphonic acid. The salt was precipitated out with cooling in an ice bath, mp. 225° C.

IR: (KBr), cm$^{-1}$: 3350, 3150, 1710, 1620, 1490, 1380, 1170, 1050 and 850.

NMR (DMSO-d$_6$): d: 2.30 (s, 3H, C$\underline{H}_3$); 2.40 (s, 3H, C$\underline{H}_3$SO$_3$H); 3.00 (m, 2H, C$\underline{H}_2$); 3.30 (m, 2H, C$\underline{H}_2$); 6.60 (s, 1H, =C$\underline{H}$); 7.00–7.40 (m, 3H, Ar—$\underline{H}$); 8.30 (bs, 2H, NH$_2$, exchangeable with D$_2$O); 11.30 (bs, NH, exchangeable with D$_2$O).

Analysis: C %, H %, N %, S % Calcd. for C$_{14}$H$_{19}$N$_3$O$_4$S: 51.69, 5.84, 12.92, 9.84 Found: 51.36, 5.76, 12.20, 9.45

Pharmacological methods to evaluate Antiarrhythmic and Cardioprotective action:

Sodium -Proton exchange inhibition in rabbit erythrocytes:

Albino rabbits of New Zealand strain were fed with 2% cholesterol diet for six weeks prior to collecting blood for the determination of Na$^+$/H$^+$ exchanger activity in the erythrocytes. Hypercholesteremia has been reported to increase the exchanger activity in the rabbit erythrocytes (Scholz et al, 1990; Arteriosklerose-Neue Aspekte aus Zellbiologie und Molekulargenetik, Epidemiologie und Klinik; Assmann, G. et al, Eds, Braunschweig, Wiesbaden, Vieweg, 296–302). Blood samples were collected from the ear vein and hematocrit was determined. About 200 ml of blood was incubated at 37° C. for 1 hour with hyperosmolar sucrose buffer containing 0.1 mmoles Ouabain in the presence and absence of test sample. After the incubation period, the reaction was stopped by addition of 5 ml of ice cold $MgCl_2$ solution containing 0.1 mmole Ouabain. The erythrocytes were washed three times with 5 ml quantities of $MgCl_2$ solution. They were hemolyzed by the addition of 4 ml of distilled water and the sodium content of the hemolyzate was determined by flame-photometry. The activity of the test compound was determined by its ability to reduce the sodium content of the erythrocyte and was expressed as $IC_{50}$ which is the concentration necessary to reduce the erythrocyte sodium content to 50%.

TABLE 2

| Compound No. | $IC_{50}$ (M) |
| --- | --- |
| 4 | 0.70 |
| 6 | 0.66 |
| 7 | 0.45 |

What is claimed is:

1. An Indanylidineacetylguanidine of formula I

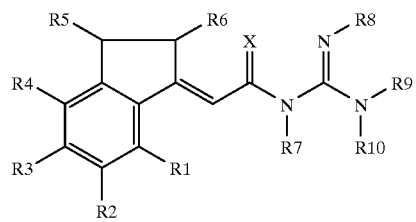

wherein,

R1, R2, R3, R4, R5 and R6 individually or collectively are H, $C_1$–$C_{10}$-alkyl; haloalkyl having 1–6 carbon atoms, O—$C_1$–$C_{10}$-alkyl, haloalkoxy having 1–6 carbon atoms, F, Cl, Br, l, aryl, substituted aryl, OH, O-lower alkyl, O-aryl, O-lower alkyl aryl, O-substituted aryl, O-lower alkyl-substituted aryl, $NO_2$, CN, $CF_3$, $NH_2$, $SO_3H$, $SO_2$-alkyl or $SO_2$-alkylaryl;

X is O: and

R7, R8, R9 and R10 are hydrogen.

2. A process for the preparation of a compound according to clam 1, which comprises reacting a compound of formula V

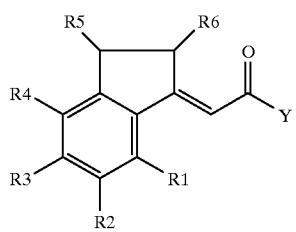

in which

R1, R2, R3, R4, R5 and R6 are as defined in claim 1 and Y is a leaving group selected from —O—($C_1$–$C_4$)-alkyl, halogen or imidazolyl, with a guanidine of formula VI,

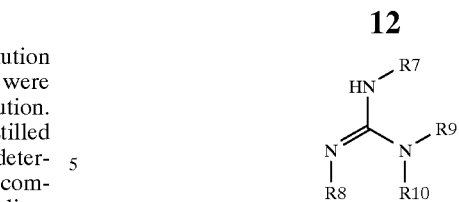

wherein R7, R8, R9 and R10 are defined as in claim 1, and if desired converting the product into the pharmaceutically tolerated salts.

3. A method of treating cardiac arrhythmias comprising administering to a patient an effective amount of a compound according to claim 1.

4. A method of treating cardiac infarction comprising administering to a patient an effective amount of a compound according to claim 1.

5. A method of treating angina pectoris comprising administering to a patient an effective amount of a compound according to claim 1.

6. A method of treating ischemic states of the heart comprising administering to a patient an effective amount of a compound according to claim 1.

7. A method of treating ischemic states of the peripheral and central nervous system and of apoplexy comprising administering to a patient an effective amount of a compound according to claim 1.

8. A method of treating ischemic states of peripheral organs and extremities comprising administering to a patient an effective amount of a compound according to claim 1.

9. A method of treating shock states comprising administering to a patient an effective amount of a compound according to claim 1.

10. A method of preparing a medicament for employment in surgical operations and organ transplantations comprising a compound according to claim 1.

11. A method of preparing a medicament for the preservation and storage of transplants for surgical measures comprising a compound according to claim 1.

12. A method of preparing a medicament for the treatment of diseases in which cell proliferation is a primary or secondary cause, and therefore its use as a antiatherosclerotic or as an agent against delayed diabetic complications, cancer diseases, fibrotic diseases, such as pulmonary fibrosis, hepatic fibrosis or renal fibrosis, and prostate hyperplasia comprising a compound according to claim 1.

13. A method of preparing a scientific tool for the inhibition of the $Na^+/H^+$exchanger and for the diagnosis of hypertension and proliferative diseases comprising a compound according to claim 1.

14. A method preparing a medicament for the treatment or prophylaxis of disorders of lipid metabolism comprising a compound according to claim 1.

15. A medicine comprising an effective amount of a compound according to claim 1.

* * * * *

UNITED STATES PATENT AND TRADEMARK OFFICE
CERTIFICATE OF CORRECTION

PATENT NO. : 5,900,436
DATED : May 4, 1999
INVENTOR(S) : Nirogi Ramakrishna et al.

It is certified that error appears in the above-identified patent and that said Letters Patent is hereby corrected as shown below:

<u>Column 11, claim 1,</u>
Line 36, change "1" to -- I --;
Line 40, change "O:" to -- O; --.

Signed and Sealed this

Twenty-sixth Day of February, 2002

Attest:

JAMES E. ROGAN
Attesting Officer  Director of the United States Patent and Trademark Office